United States Patent
Helber et al.

(10) Patent No.: US 6,885,026 B1
(45) Date of Patent: Apr. 26, 2005

(54) ORGANIC ELEMENT FOR ELECTROLUMINESCENT DEVICES

(75) Inventors: Margaret J. Helber, Webster, NY (US); J. Ramon Vargas, Webster, NY (US)

(73) Assignee: Eastman Kodak Company, Rochester, NY (US)

( * ) Notice: Subject to any disclaimer, the term of this patent is extended or adjusted under 35 U.S.C. 154(b) by 0 days.

(21) Appl. No.: 10/768,776

(22) Filed: Jan. 30, 2004

(51) Int. Cl.$^7$ .............................................. H01L 35/24
(52) U.S. Cl. ..................... 257/40; 257/103; 428/917; 313/504; 252/301.26
(58) Field of Search .................. 257/40, 103; 428/917; 313/504; 252/301.26

(56) References Cited

U.S. PATENT DOCUMENTS

| | | | |
|---|---|---|---|
| 4,774,339 | A |  9/1988 | Haugland et al. |
| 5,683,823 | A | 11/1997 | Shi et al. |
| 6,661,023 | B1 | 12/2003 | Hoag et al. |
| 6,689,494 | B1 * | 2/2004 | Karandikar ................. 428/690 |
| 6,824,893 | B1 * | 11/2004 | Hoag et al. ................. 428/690 |
| 2003/0198829 | A1 | 10/2003 | Hoag et al. |

FOREIGN PATENT DOCUMENTS

| | | |
|---|---|---|
| EP | 0 046 861 | 1/1984 |
| EP | 0 747 448 | 11/2002 |
| JP | 9-289081 | 11/1997 |
| JP | 11-97180 | 4/1999 |
| JP | 2001-294851 | 10/2001 |

OTHER PUBLICATIONS

M. J. Helber, et al., "Organic Elemlent for Electroluminescent Devices", U.S. Appl. No. 10/ , (D–87138) filed Jan. 30, 2004.

M. J. Helber, et al., "Organic Element for Electroluminescent Devices", U.S. Appl. No. 10/ , (D–87137) filed Jan. 30, 2004.

J. R. Vargas, et al., "Organic Element for Electroluminescent Devices", U.S. Appl. No. (10/ , (D–86131) filed Jan. 30, 2004.

* cited by examiner

*Primary Examiner*—Sara Crane
(74) *Attorney, Agent, or Firm*—Arthur E. Kluegel

(57) ABSTRACT

Disclosed is an electroluminescent device comprising a light emitting layer comprising a boron complex wherein the boron is bonded to a nitrogen atom of a 6-membered heteroaromatic ring group and to a nitrogen atom of a 5-membered heteroaromatic ring group, provided that the 5- and 6-membered heteroaromatic ring groups are further connected by a methene bridge, and provided further that the 5-membered heteroaromatic ring contains at least one additional heteroatom that is divalent or trivalent. Also disclosed is a device containing the electroluminescent device and a process for emitting light using the device.

28 Claims, 1 Drawing Sheet

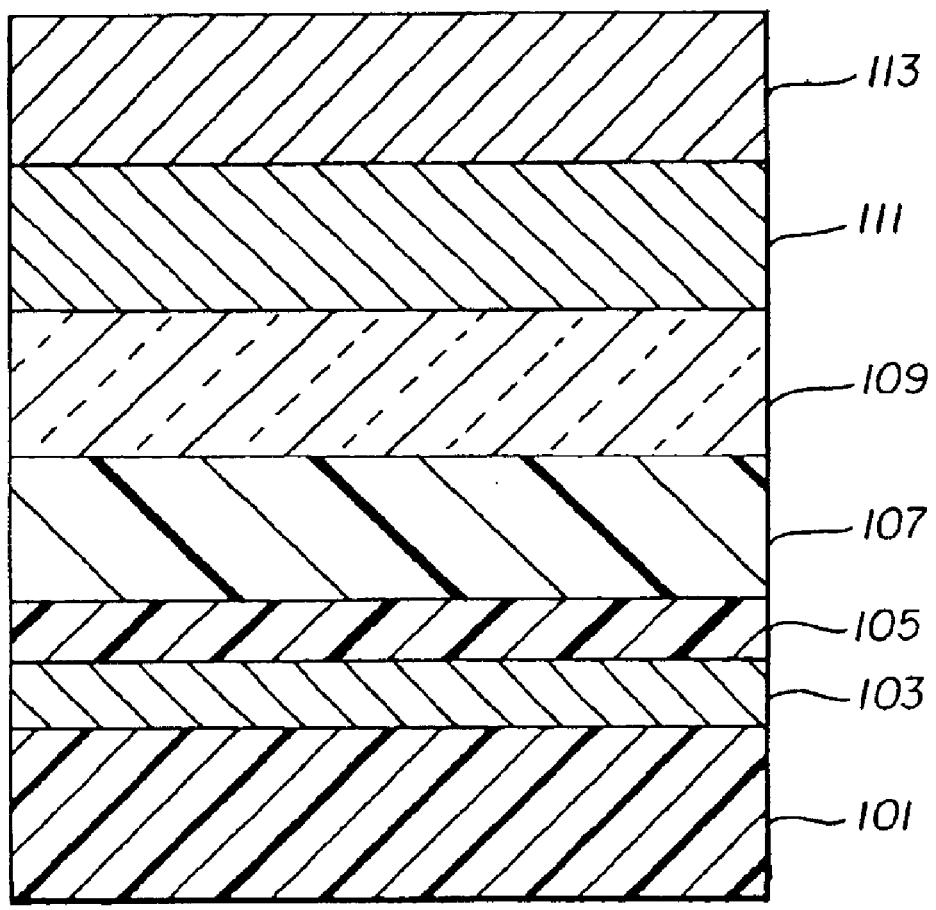

ORGANIC ELEMENT FOR ELECTROLUMINESCENT DEVICES

FIELD OF THE INVENTION

This invention relates to an electroluminescent (EL) device comprising a light-emitting layer comprising a boron complex that can provide a wide range of hues.

BACKGROUND OF THE INVENTION

While organic electroluminescent (EL) devices have been known for over two decades, their performance limitations have represented a barrier to many desirable applications. In simplest form, an organic EL device is comprised of an anode for hole injection, a cathode for electron injection, and an organic medium sandwiched between these electrodes to support charge recombination that yields emission of light. These devices are also commonly referred to as organic light-emitting diodes, or OLEDs. Representative of earlier organic EL devices are Gurnee et al. U.S. Pat. No. 3,172,862, issued Mar. 9, 1965; Gurnee U.S. Pat. No. 3,173,050, issued Mar. 9, 1965; Dresner, "Double Injection Electroluminescence in Anthracene", RCA Review, Vol. 30, pp. 322–334, 1969; and Dresner U.S. Pat. No. 3,710,167, issued Jan. 9, 1973. The organic layers in these devices, usually composed of a polycyclic aromatic hydrocarbon, were very thick (much greater than 1 Sun). Consequently, operating voltages were very high, often>100V.

More recent organic EL devices include an organic EL element consisting of extremely thin layers (e.g. <1.0 $\mu$m) between the anode and the cathode. Herein, the term "organic EL element" encompasses the layers between the anode and cathode. Reducing the thickness has lowered the resistance of the organic layer and has enabled devices that operate at much lower voltage. In a basic two-layer EL device structure, described first in U.S. Pat. No. 4,356,429, one organic layer of the EL element adjacent to the anode is specifically chosen to transport holes, and therefore, it is referred to as the hole-transporting layer, and the other organic layer is specifically chosen to transport electrons, and is referred to as the electron-transporting layer. Recombination of the injected holes and electrons within the organic EL element results in efficient electroluminescence.

There have also been proposed three-layer organic EL devices that contain an organic light-emitting layer (LEL) between the hole-transporting layer and electron-transporting layer, such as that disclosed by Tang et al (*J. Applied Physics,* 65, Pages 3610–3616, (1989)). The light-emitting layer commonly consists of a host material doped with a guest material, also known as a dopant. Still further, there has been proposed in U.S. Pat. No. 4,769,292 a four-layer EL element comprising a hole-injecting layer (HTL), a hole-transporting layer (HTL), a light-emitting layer (LEL) and an electron transport/injection layer (ETL). These structures have resulted in improved device efficiency.

Since these early inventions, further improvements in device materials have resulted in improved performance in attributes such as color, stability, luminance efficiency and manufacturability, e.g., as disclosed in U.S. Pat. No. 5,061,569, U.S. Pat. No. 5,409,783, U.S. Pat. No. 5,554,450, U.S. Pat. No. 5,593,788, U.S. Pat. No. 5,683,823, U.S. Pat. No. 5,908,581, U.S. Pat. No. 5,928,802, U.S. Pat. No. 6,020,078, and U.S. Pat. No. 6,208,077, amongst others.

Notwithstanding these developments, there are continuing needs for organic EL device components, such as light-emitting materials, sometimes referred to as dopants, that will provide high luminance efficiencies combined with high color purity and long lifetimes. In particular, there is a need to be able to adjust the emission wavelength of the light-emitting material for various applications. For example, in addition to the need for blue, green, and red light-emitting materials there is a need for blue-green, yellow and orange light-emitting materials in order to formulate white-light emitting electroluminescent devices. For example, a device can emit white light by emitting a combination of colors, such as blue-green light and red light or a combination of blue light and orange light.

White EL devices can be used with color filters in full-color display devices. They can also be used with color filters in other multicolor or functional-color display devices. White EL devices for use in such display devices are easy to manufacture, and they produce reliable white light in each pixel of the displays. Although the OLEDs are referred to as white and can appear white or off-white, for this application, the CIE coordinates of the light emitted by the OLED are less important than the requirement that the spectral components passed by each of the color filters be present with sufficient intensity in that light. The devices must also have good stability in long-term operation. That is, as the devices are operated for extended periods of time, the luminance of the devices should decrease as little as possible.

Boron complexes have been used as labeling dyes in analytical and biological applications; for example, see EP 4,774,339, EP 747,448 and EP 46, 861. However, boron complexes have found only limited application as dopants in electroluminescent devices. In one example, a useful class of dopants is derived from the 5,6,5-tricyclic pyrromethene-BF$_2$ complexes and disclosed in U.S. Pat. No. 5,683,823; JP 09 289,081A; and JP 11 097,180A. These materials are characterized by typically narrow emission spectra, which may result in attractively high color purity. However, the green emitting unsubstituted or alkyl substituted pyrromethene-BF$_2$ complexes exhibit relatively low quantum efficiencies of electroluminescence. In order to achieve highly efficient OLEDs, one needs to use phenyl rings as substituents thereby extending the conjugated $\pi$-system. As a result, the emission wavelength typically becomes red-shifted yielding a reddish amber color, which is the shortest wavelength light that can be emitted by pyrromethene-BF2 complexes with good efficiency. In simple terms, luminance efficient green or blue-green OLEDs do not appear to be conveniently obtained with pyrromethene BF$_2$ complexes used as dopants.

JP2001294851 A describes boron complexes of heterocycles used in an electroluminescent device. For example, it describes materials in which one ring includes a cyclic amide or sulfonamide. However, these materials are reported to afford a narrow emission spectrum, which would not necessarily be desirable for use in a white-light-emitting device, which must emit a broad spectrum of light. Also, in some cases these materials were not very efficient at emitting light.

U.S. Pat. No. 6,661,023 B2 describes electroluminescent (EL) device containing a boron dopant compound containing a bis(azinyl)methene boron complex. Such compounds, however, can be inefficient in their quantum efficiency of emission. The use of these materials is also limited by the difficulty in tuning the emission wavelengths, for example, to obtain a blue-green emission. Certain boron complex containing devices are described in U.S. Pat. No. 6,661,023 B2 to Benjamin P. Hoag et al. and in patent publication US 2003-0198829 A1 to Benjamin P. Hoag et al.

It is a problem to be solved to provide a material for a light-emitting layer of an OLED device that exhibits high luminance efficiency and whose structure can be easily modified so as to adjust the emission wavelengths and particularly whose structure can be modified so that it emits in the blue-green region.

SUMMARY OF THE INVENTION

The invention provides an electroluminescent device comprising a light emitting layer comprising a boron complex wherein the boron is bonded to a nitrogen atom of a 6-membered heteroaromatic ring group and to a nitrogen atom of a 5-membered heteroaromatic ring group, provided that the 5- and 6-membered heteroaromatic ring groups are further connected by a methene bridge, and provided further that the 5-membered heteroaromatic ring contains at least one additional heteroatom that is divalent or trivalent. The invention also provides a device containing the electroluminescent device and a process for emitting light using the device.

The invention device exhibits improve efficiency and emission hue

BRIEF DESCRIPTION OF THE DRAWINGS

FIG. 1 shows a schematic cross-section of a typical OLED device in which this invention may be used.

DETAILED DESCRIPTION OF THE INVENTION

An electroluminescent device of the invention may be a multilayer device comprising a cathode, an anode, charge-injecting layers (if necessary), charge-transporting layers, and a light-emitting layer (LEL) comprising a host and at least one light-emitting material. Desirably the light emitting layer comprises a boron complex wherein the boron is bonded to a nitrogen atom of a 6-membered heteroaromatic ring group and a nitrogen atom of a 5-membered heteroaromatic ring group and provided that the 5- and 6-membered rings are further connected by a methene group which may be referred to as a bridge, and provided the 5-membered ring contains at least one additional heteroatom that is divalent or trivalent. In one suitable embodiment the additional heteroatom is a N, O, S, Se, or Te atom. In another suitable embodiment the additional heteroatom is an N, O or S atom.

In one desirable embodiment the five-membered ring is fused to an additional aromatic ring group, such as a benzene ring group. Suitably the five-membered ring is fused to an additional aromatic ring group and the six-membered ring is also fused to an additional, independently selected, aromatic ring group.

The methene bridge may be substituted or unsubstituted. In one suitable embodiment the methene bridge is substituted with cyano substituent, a trifluoromethyl substituent, an aryl group, such as a phenyl group or a tolyl group, a heteroaryl group, such as a pyridine group, or an alkyl group, such as a methyl group.

In one desirable embodiment the boron complex is represented by Formula (1).

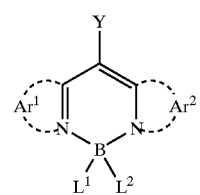

(1)

In Formula (1), $Ar^1$ represents the atoms necessary to form a six-membered heteroaromatic ring group. Examples of such ring groups are pyridine ring groups, pyrazine ring groups, pyridazine ring groups, quinoline ring groups, and isoquinoline ring groups.

$Ar^2$ represents the atoms necessary to form a five-membered heteroaromatic ring that contains, in addition to the nitrogen atom, at least one additional heteroatom that is divalent or trivalent. Examples of suitable ring groups are a thiazole ring group, a selenazole ring group, an imidazole ring group, an oxazole ring group, a pyrazole ring group, a benzothiazole ring group, a benzoselenazole ring group, a benzimidazole ring group, and a benzoxazole ring group.

The rings formed by $Ar^1$ and $Ar^2$ may contain additional fused rings. For example $Ar^1$ and $Ar^2$ may be fused with independently selected benzene ring groups. In one suitable embodiment the substituents of Formula (I) are chosen so that at least six rings are present.

$L^1$ and $L^2$ represent independently selected substituents. For illustrative examples, $L^1$ and $L^2$ can each independently represent a halogen substituent, an alkyl group, an aryl group, an alkoxy group, an alkylthio group, an arylthio group, a sulfamoyl group, an acetamido group, a diarylamino group, and an aryloxy group. In one desirable embodiment $L^1$ and $L^2$ represent independently a fluoro substituent or an alkyl carboxylate group, such as an acetate group or propionate group. In one desirable embodiment $L^1$ and $L^2$ both represent a fluoro substituent.

Y represents hydrogen or a substituent. For example Y may represent a cyano substituent, an aryl group, such as a phenyl group or a tolyl group, a heteroaryl group, such as a pyridine group, or an alkyl group, such as a methyl group.

In one preferred embodiment substituents of Formula (1) are selected to prevent or limit exciplex formation. That is, substituents are chosen that inhibit the formation of excited state complexes involving one or more compounds of Formula (1). Particularly useful substituents introduce steric interactions, such as one or more t-butyl groups, s-pentyl groups, or mesityl groups.

In one desirable embodiment Formula (2) represents the boron complex.

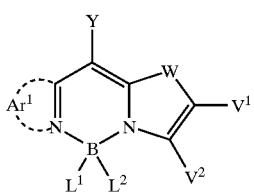

(2)

In Formula (2), W represents O, S, Se, Te or $N-R^a$, wherein $R^a$ is a substituent, such as a methyl group or a phenyl group. $V^1$ and $V^2$ independently represent hydrogen or an independently selected substituent, for example an alkyl group, such as a methyl group, or an aryl group, such as a phenyl group. $V^1$ and $V^2$ may join together to form a ring group such as a benzene ring group. $Ar^1$, $L^1$ $L^2$, and Y were described previously.

In one desirable embodiment the boron complex is represented by Formula (3).

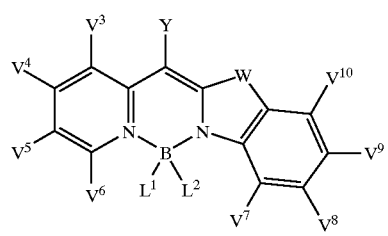

(3)

In Formula (3), $V^3$–$V^{10}$ independently represent hydrogen or an independently selected substituent, such as a phenyl group or a methyl group. Adjacent substituents may join together to form a ring group, such as a benzene ring group. W, $L^1$, $L^2$, and Y were described previously.

In another suitable embodiment the substituents of Formula (1) are selected to provide an emission in the range of 450–500 nm. In one desirable embodiment the substituents of Formula (1) are selected to provide an emission in the range of 460–490 nm.

In one suitable embodiment the substituents of Formula (1) are selected to provide an emission that has a primary maximum and a secondary maximum. In one desirable embodiment, one maximum is in the region of 460 to 470 nm and another maximum is in the region of 485 to 495 nm.

Suitably, the light-emitting layer of the device comprises a host and one or more light-emitting materials where the light-emitting material(s) is present in an amount of up to 10 wt % of the host, more typically from 0.1–5.0 wt % of the host. At least one light-emitting material is suitably a boron complex comprising a ring system of Formula (1).

Desirable hosts include those based on a chelated oxinoid compound or an anthracene compound. In one desirable embodiment the host is represented by Formula (4).

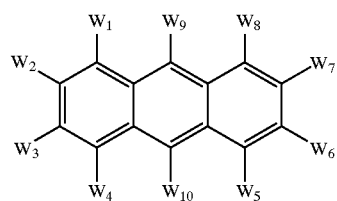

(4)

In Formula (4), $W_1$–$W_{10}$ independently represent hydrogen or an independently selected substituent, provided that two adjacent substituents can combine to form rings. In one suitable embodiment, $W^9$ and $W^{10}$ independently represent naphthyl groups. In another desirable embodiment, $W^9$ and $W^{10}$ represent a naphthyl group and a biphenyl group.

Particular examples of hosts are tris(8-quinolinolato) aluminum (III), 9,10-di-(2-naphthyl)anthracene, 2-tert-butyl-9,10-di-(2-naphthyl)anthracene, 9-(4-biphenyl)-10-(2-naphthyl)anthracene and 9-(4-biphenyl)-10-(1-naphthyl) anthracene. Preferably, the host is selected such that the host absorbs light at a shorter wavelength than the dopant and the emission spectrum of the host overlaps with the absorption spectrum of the dopant.

Embodiments of the dopants useful in the invention can provide a wide range of hues. Embodiments of the dopants especially useful in the invention provide an emitted light having a blue hue, a green hue or a blue-green hue. In another preferred embodiment, dopants useful in the invention are used in an electroluminescent device that emits white light.

Useful boron complexes can be synthesized by methods known in the literature. Desirably a suitable ligand is prepared and the ligand is then complexed to boron. For examples of boron complexation reactions see G, Sathyamoorthi, M. Soong, T. Ross, J. Boyer, *Heteroatom Chem.*, 4, 603 (1993) and J. Douglass, P. Barelski, R. Blankenship, *J. Heterocycl. Chem.*, 10, 255 (1973).

Illustrative examples of boron complexes useful in the present invention include the following compounds.

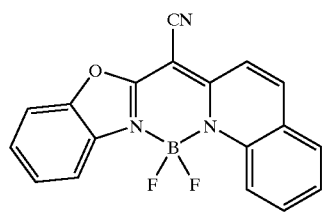

Inv-1

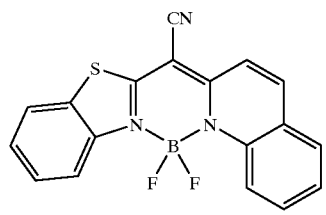

Inv-2

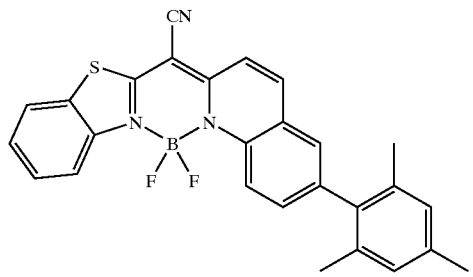

Inv-3

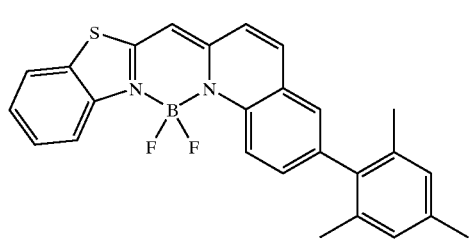

Inv-4

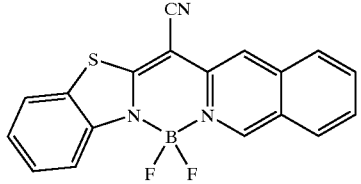

Inv-5

Inv-6
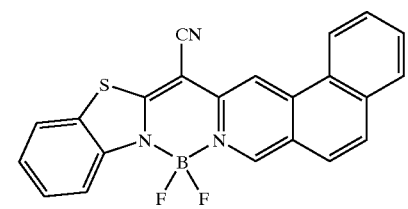
Inv-7
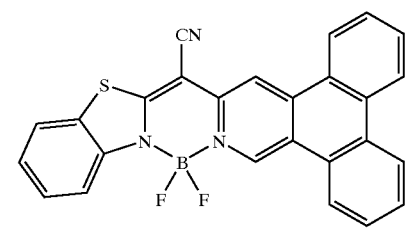
Inv-8
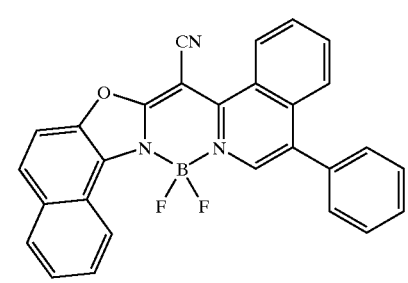
Inv-9
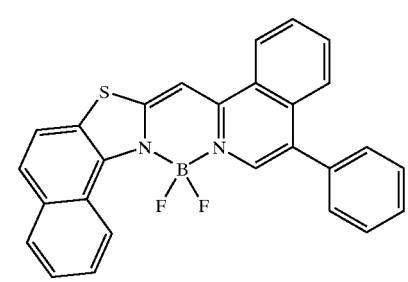
Inv-10
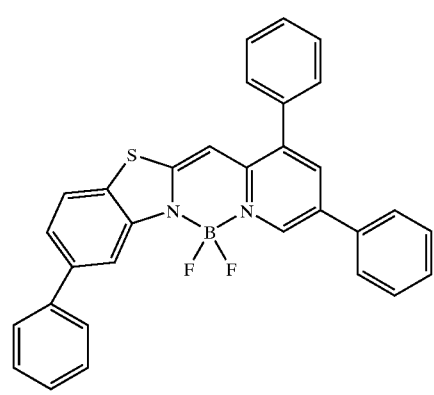
Inv-11
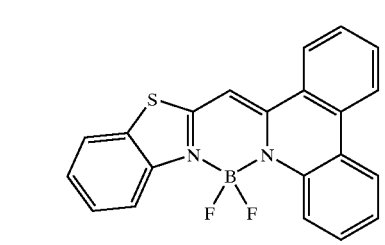
Inv-12
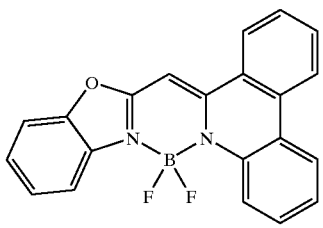
Inv-13
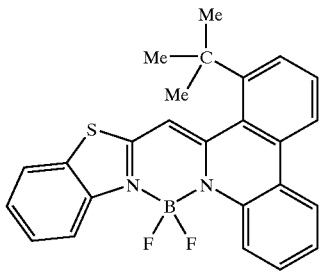
Inv-14
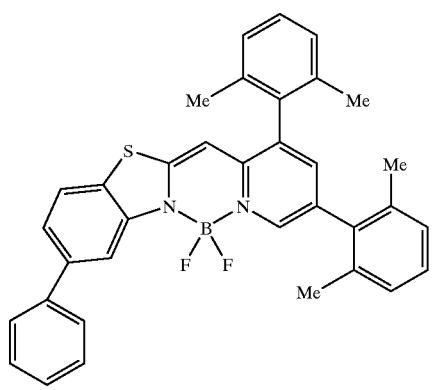
Inv-15
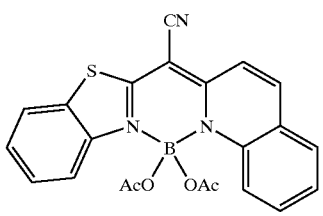
Inv-16
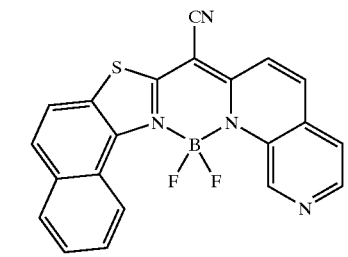
Inv-17
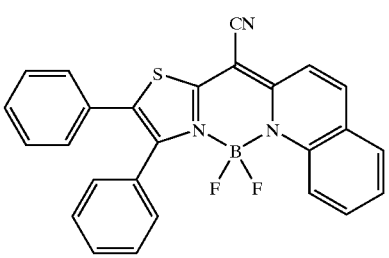

Inv-18
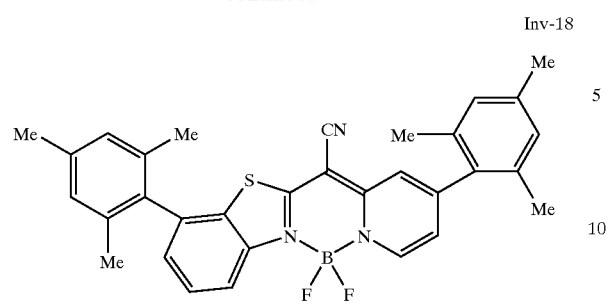
Inv-19
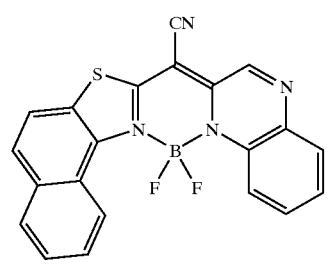
Inv-20
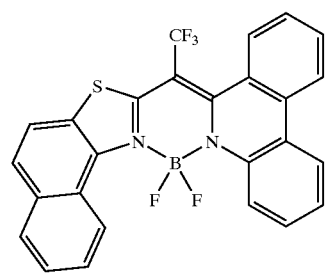
Inv-21
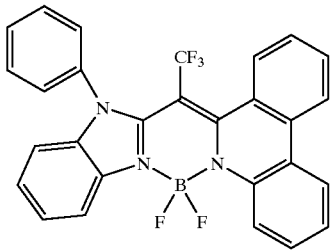
Inv-22
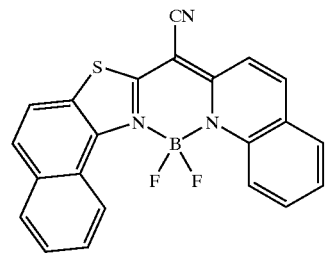
Inv-23
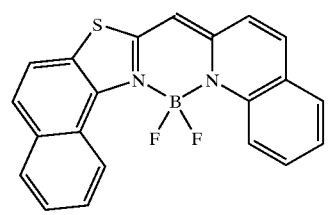
Inv-24
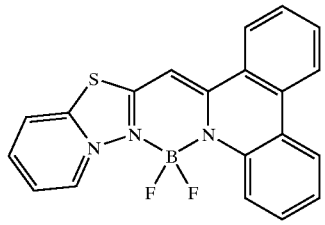
Inv-25
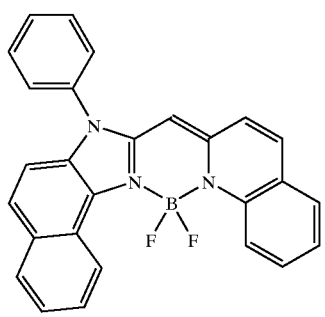
Inv-26
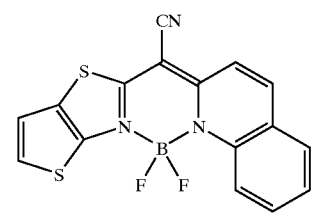
Inv-27
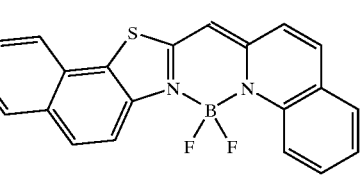
Inv-28
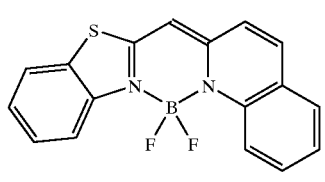
Inv-29
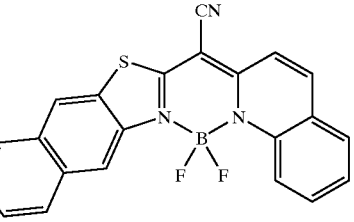
Inv-30
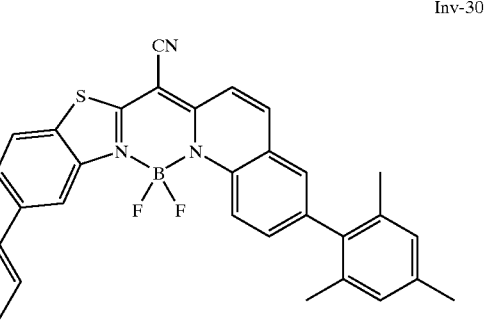

-continued

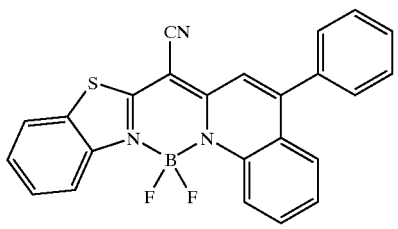

Inv-31

Embodiments of the invention provide not only improved luminance efficiency but also a desirable blue or blue-green hue as evidenced by the location and shape of the emission curve of the emitted light.

Unless otherwise specifically stated, use of the term "substituted" or "substituent" means any group or atom other than hydrogen. Additionally, when the term "group" is used, it means that when a substituent group contains a substitutable hydrogen, it is also intended to encompass not only the substituent's unsubstituted form, but also its form further substituted with any substituent group or groups as herein mentioned, so long as the substituent does not destroy properties necessary for device utility. Suitably, a substituent group may be halogen or may be bonded to the remainder of the molecule by an atom of carbon, silicon, oxygen, nitrogen, phosphorous, sulfur, selenium, or boron. The substituent may be, for example, halogen, such as chloro, bromo or fluoro; nitro; hydroxyl; cyano; carboxyl; or groups which may be further substituted, such as alkyl, including straight or branched chain or cyclic alkyl, such as methyl, trifluoromethyl, ethyl, t-butyl, 3-(2,4-di-t-pentylphenoxy) propyl, and tetradecyl; alkenyl, such as ethylene, 2-butene; alkoxy, such as methoxy, ethoxy, propoxy, butoxy, 2-methoxyethoxy, sec-butoxy, hexyloxy, 2-ethylhexyloxy, tetradecyloxy, 2-(2,4-di-t-pentylphenoxy)ethoxy, and 2-dodecyloxyethoxy; aryl such as phenyl, 4-t-butylphenyl, 2,4,6-trimethylphenyl, naphthyl; aryloxy, such as phenoxy, 2-methylphenoxy, alpha- or beta-naphthyloxy, and 4-tolyloxy; carbonamido, such as acetamido, benzamido, butyramido, tetradecanamido, alpha-(2,4-di-t-pentyl-phenoxy)acetamido, alpha-(2,4-di-t-pentylphenoxy) butyramido, alpha-(3-pentadecylphenoxy)-hexanamido, alpha-(4-hydroxy-3-t-butylphenoxy)-tetradecanamido, 2-oxo-pyrrolidin-1-yl, 2-oxo-5-tetradecylpyrrolin-1-yl, N-methyltetradecanamido, N-succinimido, N-phthalimido, 2,5-dioxo-1-oxazolidinyl, 3-dodecyl-2,5-dioxo-1-imidazolyl, and N-acetyl-N-dodecylamino, ethoxycarbonylamino, phenoxycarbonylamino, benzyloxycarbonylamino, hexadecyloxycarbonylamino, 2,4-di-t-butylphenoxycarbonylamino, phenylcarbonylamino, 2,5-(di-t-pentylphenyl) carbonylamino, p-dodecyl-phenylcarbonylamino, p-tolylcarbonylamino, N-methylureido, N,N-dimethylureido, N-methyl-N-dodecylureido, N-hexadecylureido, N,N-dioctadecylureido, N,N-dioctyl-N'-ethylureido, N-phenylureido, N,N-diphenylureido, N-phenyl-N-p-tolylureido, N-(m-hexadecylphenyl)ureido, N,N-(2,5-di-t-pentylphenyl)-N'-ethylureido, and t-butylcarbonamido; sulfonamido, such as methylsulfonamido, benzenesulfonamido, p-tolylsulfonamido, p-dodecylbenzenesulfonamido, N-methyltetradecylsulfonamido, N,N-dipropyl-sulfamoylamino, and hexadecylsulfonamido; sulfamoyl, such as N-methylsulfamoyl, N-ethylsulfamoyl, N,N-dipropylsulfamoyl, N-hexadecylsulfamoyl, N,N-dimetylsulfamoyl, N-[3-(dodecyloxy)propyl]sulfamoyl, N-[4-(2,4-di-t-pentylphenoxy)butyl]sulfamoyl, N-methyl-N-tetradecylsulfamoyl, and N-dodecylsulfamoyl; carbamoyl, such as N-methylcarbamoyl, N,N-butylcarbamoyl, N-octadecylcarbamoyl, N-[4-(2,4-di-t-pentylphenoxy)butyl]carbamoyl, N-methyl-N-tetradecylcarbamoyl, and N,N-dioctylcarbamoyl; acyl, such as acetyl, (2,4-di-t-amylphenoxy)acetyl, phenoxycarbonyl, p-dodecyloxyphenoxycarbonyl methoxycarbonyl, butoxycarbonyl, tetradecyloxycarbonyl, ethoxycarbonyl, benzyloxycarbonyl, 3-pentadecyloxycarbonyl, and dodecyloxycarbonyl; sulfonyl, such as methoxysulfonyl, octyloxysulfonyl, tetradecyloxysulfonyl, 2-ethylhexyloxysulfonyl, phenoxysulfonyl, 2,4-di-t-pentylphenoxysulfonyl, methylsulfonyl, octylsulfonyl, 2-ethylhexylsulfonyl, dodecylsulfonyl, hexadecylsulfonyl, phenylsulfonyl, 4-nonylphenylsulfonyl, and p-tolylsulfonyl; sulfonyloxy, such as dodecylsulfonyloxy, and hexadecylsulfonyloxy; sulfinyl, such as methylsulfinyl, octylsulfinyl, 2-ethylhexylsulfinyl, dodecylsulfinyl, hexadecylsulfinyl, phenylsulfinyl, 4-nonylphenylsulfinyl, and p-tolylsulfinyl; thio, such as ethylthio, octylthio, benzylthio, tetradecylthio, 2-(2,4-di-t-pentylphenoxy)ethylthio, phenylthio, 2-butoxy-5-t-octylphenylthio, and p-tolylthio; acyloxy, such as acetyloxy, benzoyloxy, octadecanoyloxy, p-dodecylamidobenzoyloxy, N-phenylcarbamoyloxy, N-ethylcarbamoyloxy, and cyclohexylcarbonyloxy; amine, such as phenylanilino, 2-chloroanilino, diethylamine, dodecylamine; imino, such as 1 (N-phenylimido)ethyl, N-succinimido or 3-benzylhydantoinyl; phosphate, such as dimethylphosphate and ethylbutylphosphate; phosphite, such as diethyl and dihexyiphosphite; a heterocyclic group, a heterocyclic oxy group or a heterocyclic thio group, each of which may be substituted and which contain a 3 to 7 membered hetero cyclic ring composed of carbon atoms and at least one hetero atom selected from the group consisting of oxygen, nitrogen, sulfur, phosphorous, or boron, such as 2-furyl, 2-thienyl, 2-benzimidazolyloxy or 2-benzothiazolyl; quaternary ammonium, such as triethylamimonium; quaternary phosphonium, such as triphenylphosphonium; and silyloxy, such as trimethylsilyloxy.

If desired, the substituents may themselves be further substituted one or more times with the described substituent groups. The particular substituents used may be selected by those skilled in the art to attain the desired desirable properties for a specific application and can include, for example, electron-withdrawing groups, electron-donating groups, and steric groups. When a molecule may have two or more substituents, the substituents may be joined together to form a ring such as a fused ring unless otherwise provided. Generally, the above groups and substituents thereof may include those having up to 48 carbon atoms, typically 1 to 36 carbon atoms and usually less than 24 carbon atoms, but greater numbers are possible depending on the particular substituents selected.

General Device Architecture

The present invention can be employed in many EL device configurations using small molecule materials, oligomeric materials, polymeric materials, or combinations thereof. These include very simple structures comprising a single anode and cathode to more complex devices, such as passive matrix displays comprised of orthogonal arrays of anodes and cathodes to form pixels, and active-matrix displays where each pixel is controlled independently, for example, with thin film transistors (TFTs).

There are numerous configurations of the organic layers wherein the present invention can be successfully practiced.

The essential requirements of an OLED are an anode, a cathode, and an organic light-emitting layer located between the anode and cathode. Additional layers may be employed as more fully described hereafter.

A typical structure according to the present invention and especially useful for a small molecule device, is shown in FIG. 1 and is comprised of a substrate 101, an anode 103, a hole-injecting layer 105, a hole-transporting layer 107, a light-emitting layer 109, an electron-transporting layer 111, and a cathode 113. These layers are described in detail below. Note that the substrate 101 may alternatively be located adjacent to the cathode 113, or the substrate 101 may actually constitute the anode 103 or cathode 113. The organic layers between the anode 103 and cathode 113 are conveniently referred to as the organic EL element. Also, the total combined thickness of the organic layers is desirably less than 500 nm. If the device includes phosphorescent material, a hole-blocking layer, located between the light-emitting layer and the electron-transporting layer, may be present.

The anode 103 and cathode 113 of the OLED are connected to a voltage/current source through electrical conductors. The OLED is operated by applying a potential between the anode 103 and cathode 113 such that the anode 103 is at a more positive potential than the cathode 113. Holes are injected into the organic EL element from the anode 103 and electrons are injected into the organic EL element at the cathode 113. Enhanced device stability can sometimes be achieved when the OLED is operated in an AC mode where, for some time period in the AC cycle, the potential bias is reversed and no current flows. An example of an AC driven OLED is described in U.S. Pat. No. 5,552,678.

Substrate

The OLED device of this invention is typically provided over a supporting substrate 101 where either the cathode 113 or anode 103 can be in contact with the substrate. The electrode in contact with the substrate 101 is conveniently referred to as the bottom electrode. Conventionally, the bottom electrode is the anode 103, but this invention is not limited to that configuration. The substrate 101 can either be light transmissive or opaque, depending on the intended direction of light emission. The light transmissive property is desirable for viewing the EL emission through the substrate 101. Transparent glass or plastic is commonly employed in such cases. The substrate 101 can be a complex structure comprising multiple layers of materials. This is typically the case for active matrix substrates wherein TFTs are provided below the OLED layers. It is still necessary that the substrate 101, at least in the emissive pixelated areas, be comprised of largely transparent materials such as glass or polymers. For applications where the EL emission is viewed through the top electrode, the transmissive characteristic of the bottom support is immaterial, and therefore the substrate can be light transmissive, light absorbing or light reflective. Substrates for use in this case include, but are not limited to, glass, plastic, semiconductor materials such as silicon, ceramics, and circuit board materials. Again, the substrate 101 can be a complex structure comprising multiple layers of materials such as found in active matrix TFT designs. It is necessary to provide in these device configurations a light-transparent top electrode.

Anode

When the desired electroluminescent light emission (EL) is viewed through the anode, the anode 103 should be transparent or substantially transparent to the emission of interest. Common transparent anode materials used in this invention are indium-tin oxide (ITO), indium-zinc oxide (IZO) and tin oxide, but other metal oxides can work including, but not limited to, aluminum- or indium-doped zinc oxide, magnesium-indium oxide, and nickel-tungsten oxide. In addition to these oxides, metal nitrides, such as gallium nitride, and metal selenides, such as zinc selenide, and metal sulfides, such as zinc sulfide, can be used as the anode 103. For applications where EL emission is viewed only through the cathode 113, the transmissive characteristics of the anode 103 are immaterial and any conductive material can be used, transparent, opaque or reflective. Example conductors for this application include, but are not limited to, gold, iridium, molybdenum, palladium, and platinum. Typical anode materials, transmissive or otherwise, have a work function of 4.1 eV or greater. Desired anode materials are commonly deposited by any suitable means such as evaporation, sputtering, chemical vapor deposition, or electrochemical means. Anodes can be patterned using well-known photolithographic processes. Optionally, anodes may be polished prior to application of other layers to reduce surface roughness so as to minimize short circuits or enhance reflectivity.

Cathode

When light emission is viewed solely through the anode 103, the cathode 113 used in this invention can be comprised of nearly any conductive material. Desirable materials have good film-forming properties to ensure good contact with the underlying organic layer, promote electron injection at low voltage, and have good stability. Useful cathode materials often contain a low work function metal (<4.0 eV) or metal alloy. One useful cathode material is comprised of a Mg:Ag alloy wherein the percentage of silver is in the range of 1 to 20%, as described in U.S. Pat. No. 4,885,221. Another suitable class of cathode materials includes bilayers comprising the cathode and a thin electron-injection layer (EIL) in contact with an organic layer (e.g., an electron transporting layer (ETL)), the cathode being capped with a thicker layer of a conductive metal. Here, the EIL preferably includes a low work function metal or metal salt, and if so, the thicker capping layer does not need to have a low work function. One such cathode is comprised of a thin layer of LiF followed by a thicker layer of Al as described in U.S. Pat. No. 5,677,572. An ETL material doped with an alkali metal, for example, Li-doped Alq, is another example of a useful EIL. Other useful cathode material sets include, but are not limited to, those disclosed in U.S. Pat. Nos. 5,059,861, 5,059,862, and 6,140,763.

When light emission is viewed through the cathode, the cathode 113 must be transparent or nearly transparent. For such applications, metals must be tin or one must use transparent conductive oxides, or a combination of these materials. Optically transparent cathodes have been described in more detail in U.S. Pat. No. 4,885,211, U.S. Pat. No. 5,247,190, JP 3,234,963, U.S. Pat. No. 5,703,436, U.S. Pat. No. 5,608,287, U.S. Pat. No. 5,837,391, U.S. Pat. No. 5,677,572, U.S. Pat. No. 5,776,622, U.S. Pat. No. 5,776,623, U.S. Pat. No. 5,714,838, U.S. Pat. No. 5,969,474, U.S. Pat. No. 5,739,545, U.S. Pat. No. 5,981,306, U.S. Pat. No. 6,137,223, U.S. Pat. No. 6,140,763, U.S. Pat. No. 6,172,459, EP 1 076 368, U.S. Pat. No. 6,278,236, and U.S. Pat. No. 6,284,3936. Cathode materials are typically deposited by any suitable method such as evaporation, sputtering, or chemical vapor deposition. When needed, patterning can be achieved through many well known methods including, but not limited to, through-mask deposition, integral shadow masking as described in U.S. Pat. No. 5,276,380 and EP 0 732 868, laser ablation, and selective chemical vapor deposition.

Hole-Injecting Layer (HIL)

A hole-injecting layer 105 may be provided between anode 103 and hole-transporting layer 107. The hole-injecting layer can serve to improve the film formation property of subsequent organic layers and to facilitate injection of holes into the hole-transporting layer 107. Suitable materials for use in the hole-injecting layer 105 include, but are not limited to, porphyrinic compounds as described in U.S. Pat. No. 4,720,432, plasma-deposited fluorocarbon polymers as described in U.S. Pat. No. 6,208,075, and some aromatic amines, for example, MTDATA (4,4',4"-tris[(3-methylphenyl)phenylamino]triphenylamine). Alternative hole-injecting materials reportedly useful in organic EL devices are described in EP 0 891 121 A1 and EP 1 029 909 A1. A hole-injection layer is conveniently used in the present invention, and is desirably a plasma-deposited fluorocarbon polymer. The thickness of a hole-injection layer containing a plasma-deposited fluorocarbon polymer can be in the range of 0.2 nm to 15 nm and suitably in the range of 0.3 to 1.5 nm.

Hole-Transporting Layer (HTL)

While not always necessary, it is often useful to include a hole-transporting layer in an OLED device. The hole-transporting layer 107 of the organic EL device contains at least one hole-transporting compound such as an aromatic tertiary amine, where the latter is understood to be a compound containing at least one trivalent nitrogen atom that is bonded only to carbon atoms, at least one of which is a member of an aromatic ring. In one form the aromatic tertiary amine can be an arylamine, such as a monoarylamine, diarylamine, triarylamine, or a polymeric arylamine. Exemplary monomeric triarylamines are illustrated by Klupfel et al. U.S. Pat. No. 3,180,730. Other suitable triarylamines substituted with one or more vinyl radicals and/or comprising at least one active hydrogen containing group are disclosed by Brantley et al U.S. Pat. No. 3,567,450 and U.S. Pat. No. 3,658,520.

A more preferred class of aromatic tertiary amines is those which include at least two aromatic tertiary amine moieties as described in U.S. Pat. No. 4,720,432 and U.S. Pat. No. 5,061,569. Such compounds include those represented by structural formula (A).

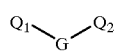

A wherein $Q_1$ and $Q_2$ are independently selected aromatic tertiary amine moieties and G is a linking group such as an arylene, cycloalkylene, or alkylene group of a carbon to carbon bond. In one embodiment, at least one of $Q_1$ or $Q_2$ contains a polycyclic fused ring structure, e.g., a naphthalene. When G is an aryl group, it is conveniently a phenylene, biphenylene, or naphthalene moiety.

A useful class of triarylamines satisfying structural formula (A) and containing two triarylamine moieties is represented by structural formula (B):

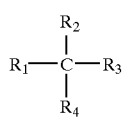

B where $R_1$ and $R_2$ each independently represents a hydrogen atom, an aryl group, or an alkyl group or $R_1$ and $R_2$ together represent the atoms completing a cycloalkyl group; and $R_3$ and $R_4$ each independently represents an aryl group, which is in turn substituted with a diaryl substituted amino group, as indicated by structural formula (C):

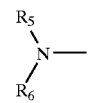

C wherein $R_5$ and $R_6$ are independently selected aryl groups. In one embodiment, at least one of $R_5$ or $R_1$ contains a polycyclic fused ring structure, e.g., a naphthalene.

Another class of aromatic tertiary amines is the tetraaryldiamines. Desirable tetraaryldiamines include two diarylamino groups, such as indicated by formula (C), linked through an arylene group. Useful tetraaryldiamines include those represented by formula (D).

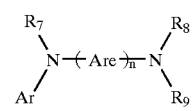

D wherein
each Are is an independently selected arylene group, such as a phenylene or anthracene moiety,
n is an integer of from 1 to 4, and
Ar, $R_7$, $R_8$, and $R_9$ are independently selected aryl groups.
In a typical embodiment, at least one of Ar, $R_7$, $R_8$, and $R_9$ is a polycyclic fused ring structure, e.g., a naphthalene.

The various alkyl, alkylene, aryl, and arylene moieties of the foregoing structural formulae (A), (B), (C), (D), can each in turn be substituted. Typical substituents include alkyl groups, alkoxy groups, aryl groups, aryloxy groups, and halide such as fluoride, chloride, and bromide. The various alkyl and alkylene moieties typically contain from about 1 to 6 carbon atoms. The cycloalkyl moieties can contain from 3 to about 10 carbon atoms, but typically contain five, six, or seven ring carbon atoms—e.g., cyclopentyl, cyclohexyl, and cycloheptyl ring structures. The aryl and arylene moieties are usually phenyl and phenylene moieties.

The hole-transporting layer can be formed of a single tertiary amine compound or a mixture of such compounds. Specifically, one may employ a triarylamine, such as a triarylamine satisfying the formula (B), in combination with a tetraaryldiamine, such as indicated by formula (D). Illustrative of useful aromatic tertiary amines are the following:
1,1-Bis(4-di-p-tolylaminophenyl)cyclohexane (TAPC)
1,1-Bis(4-di-p-tolylaminophenyl)-4-methylcyclohexane
1,1-Bis(4-di-p-tolylaminophenyl)-4-phenylcyclohexane
1,1-Bis(4-di-p-tolylaminophenyl)-3-phenylpropane (TAPPP)
N,N,N',N'-tetraphenyl-4,4'''-diamino-1,1':4', 1":4", 1'''-quaterphenyl
Bis(4-dimethylamino-2-methylphenyl)phenylmethane
1,4-bis[2-[4-[N,N-di(p-toly)amino]phenyl]vinyl]benzene (BDTAPVB)
N,N,N',N'-Tetra-p-tolyl-4,4'-diaminobiphenyl (TTB)
N,N,N',N'-Tetraphenyl-4,4'-diaminobiphenyl
N,N,N',N'-tetra-1-naphthyl-4,4'diaminobiphenyl
N,N,N',N'-tetra-2-naphthyl-4,4'-diaminobiphenyl
N-Phenylcarbazole
4,4'-Bis[N-(1-naphthyl)-N-phenylamino]biphenyl (NPB)
4,4'-Bis[N-(1-naphthyl)-N-(2-naphthyl)amino]biphenyl (TNB)

4,4'-Bis[N-(1-naphthyl)-N-phenylamino]p-terphenyl
4,4'-Bis[N-(2-naphthyl)-N-phenylamino]biphenyl
4,4'-Bis[N-(3-acenaphthenyl)-N-phenylamino]biphenyl
1,5-Bis[N-(1-naphthyl)-N-phenylamino]naphthalene
4,4'-Bis[N-(9-anthryl)-N-phenylamino]biphenyl
4,4'-Bis[N-(1-anthryl)-N-phenylamino]-p-terphenyl
4,4'-Bis[N-(2-phenanthryl)-N-phenylamino]biphenyl
4,4'-Bis[N-(8-fluoranthenyl)-N-phenylamino]biphenyl
4,4'-Bis[N-(2-pyrenyl)N-phenylamino]biphenyl
4,4'-Bis[N-(2-naphthacenyl)-N-phenylamino]biphenyl
4,4'-Bis[N-(2-perylenyl)-N-phenylamino]biphenyl
4,4'-Bis[N-(1-coronenyl)-N-phenylamino]biphenyl
2,6-Bis(di-p-tolylamino)naphthalene
2,6-Bis[di-(1-naphthyl)amino]naphthalene
2,6-Bis[N-(1-naphthyl)-N-(2-naphthyl)amino]naphthalene
N,N,N',N'-Tetra(2-naphthyl)-4,4"-diamino-p-terphenyl
4,4'-Bis{N-phenyl-N-[4-(1-naphthyl)-phenyl]amino}biphenyl
2,6-Bis[N,N-di(2-naphthyl)amino]fluorene
4,4',4"-tris[(3-methylphenyl)phenylamino]triphenylamine (MTDATA)
4,4'-Bis[N-(3-methylphenyl)N-phenylamino]biphenyl (TPD).

Another class of useful hole-transporting materials includes polycyclic aromatic compounds as described in EP 1 009 041. Tertiary aromatic amines with more than two amine groups may be used including oligomeric materials. In addition, polymeric hole-transporting materials can be used such as poly(N-vinylcarbazole) (PVK), polythiophenes, polypyrrole, polyaniline, and copolymers such as poly(3,4-ethylenedioxythiophene)/poly(4-styrenesulfonate) also called PEDOT/PSS. It is also possible for the hole-transporting layer to comprise two or more sublayers of differing compositions, the composition of each sublayer being as described above. The thickness of the hole-transporting layer can be between 10 and about 500 nm and suitably between 50 and 300 nm.

Light-Emitting Layer (LEL)

In addition to the light-emitting materials of this invention, additional light emitting materials may be used in the EL device, including other fluorescent materials. Other fluorescent materials may be used in the same layer as the boron complex material, in adjacent layers, in adjacent pixels, or any combination.

As more fully described in U.S. Pat. Nos. 4,769,292 and 5,935,721, the light-emitting layer (LEL) of the organic EL element includes a luminescent material where electroluminescence is produced as a result of electron-hole pair recombination. The light-emitting layer can be comprised of a single material, but more commonly consists of a host material doped with a guest emitting material or materials where light emission comes primarily from the emitting materials and can be of any color. The host materials in the light-emitting layer can be an electron-transporting material, as defined below, a hole-transporting material, as defined above, or another material or combination of materials that support hole-electron recombination. Fluorescent emitting materials are typically incorporated at 0.01 to 10% by weight of the host material.

The host and emitting materials can be small non-polymeric molecules or polymeric materials such as polyfluorenes and polyvinylarylenes (e.g., poly(p-phenylenevinylene), PPV). In the case of polymers, small-molecule emitting materials can be molecularly dispersed into a polymeric host, or the emitting materials can be added by copolymerizing a minor constituent into a host polymer. Host materials may be mixed together in order to improve film formation, electrical properties, light emission efficiency, operating lifetime, or manufacturability. The host may comprise a material that has good hole-transporting properties and a material that has good electron-transporting properties.

An important relationship for choosing a fluorescent material as a guest emitting material is a comparison of the excited singlet-state energies of the host and the fluorescent material. It is highly desirable that the excited singlet-state energy of the fluorescent material be lower than that of the host material. The excited singlet-state energy is defined as the difference in energy between the emitting singlet state and the ground state. For non-emissive hosts, the lowest excited state of the same electronic spin as the ground state is considered the emitting state.

Host and emitting materials known to be of use include, but are not limited to, those disclosed in U.S. Pat. No. 4,768,292, U.S. Pat. No. 5,141,671, U.S. Pat. No. 5,150,006, U.S. Pat. No. 5,151,629, U.S. Pat. No. 5,405,709, U.S. Pat. No. 5,484,922, U.S. Pat. No. 5,593,788, U.S. Pat. No. 5,645,948, U.S. Pat. No. 5,683,823, U.S. Pat. No. 5,755,999, U.S. Pat. No. 5,928,802, U.S. Pat. No. 5,935,720, U.S. Pat. No. 5,935,721, and U.S. Pat. No. 6,020,078.

Metal complexes of 8-hydroxyquinoline and similar derivatives, also known as metal-chelated oxinoid compounds (Formula E), constitute one class of useful host compounds capable of supporting electroluminescence, and are particularly suitable for light emission of wavelengths longer than 500 nm, e.g., green, yellow, orange, and red.

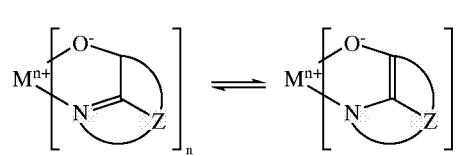

E wherein
   M represents a metal;
   n is an integer of from 1 to 4; and
   Z independently in each occurrence represents the atoms completing a nucleus having at least two fused aromatic rings.

From the foregoing it is apparent that the metal can be monovalent, divalent, trivalent, or tetravalent metal. The metal can, for example, be an alkali metal, such as lithium, sodium, or potassium; an alkaline earth metal, such as magnesium or calcium; a trivalent metal, such aluminum or gallium, or another metal such as zinc or zirconium. Generally any monovalent, divalent, trivalent, or tetravalent metal known to be a useful chelating metal can be employed.

Z completes a heterocyclic nucleus containing at least two fused aromatic rings, at least one of which is an azole or azine ring. Additional rings, including both aliphatic and aromatic rings, can be fused with the two required rings, if required. To avoid adding molecular bulk without improving on function the number of ring atoms is usually maintained at 18 or less.

Illustrative of useful chelated oxinoid compounds are the following:
   CO-1: Aluminum trisoxine [alias, tris(8-quinolinolato) aluminum(III)]
   CO-2: Magnesium bisoxine [alias, bis(8-quinolinolato) magnesium(II)]
   CO-3: Bis[benzo{f}-8-quinolinolato)zinc (II)]
   CO-4: Bis(2-methyl-8-quinolinolato)aluminum(III)-μ-oxo-bis(2-methyl-8-quinolinolato) aluminum(III)

CO-5: Indium trisoxine [alias, tris(8-quinolinolato) indium]

CO-6: Aluminum tris(5-methyloxine) [alias, tris(5-methyl-8-quinolinolato) aluminum(III)]

CO-7: Lithium oxine [alias, (8-quinolinolato)lithium(I)]

CO-8: Gallium oxine [alias, tris(8-quinolinolato)gallium (III)]

CO-9: Zirconium oxine [alias, tetra(8-quinolinolato) zirconium(IV)].

Derivatives of 9,10-di-(2-naphthyl)anthracene (Formula F) constitute one class of useful host materials capable of supporting electroluminescence, and are particularly suitable for light emission of wavelengths longer than 400 mm, e.g., blue, green, yellow, orange or red.

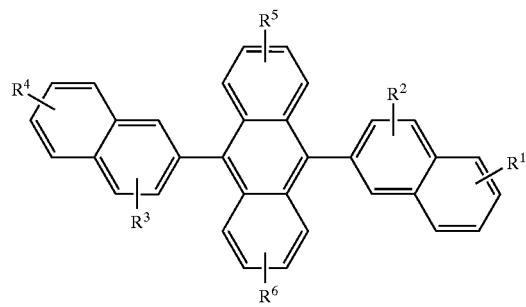

F wherein: $R^1$, $R^2$, $R^3$, $R^4$, $R^5$, and $R^6$ represent one or more substituents on each ring where each substituent is individually selected from the following groups:

Group 1: hydrogen, or alkyl of from 1 to 24 carbon atoms;

Group 2: aryl or substituted aryl of from 5 to 20 carbon atoms;

Group 3: carbon atoms from 4 to 24 necessary to complete a fused aromatic ring of anthracenyl; pyrenyl, or perylenyl;

Group 4: heteroaryl or substituted heteroaryl of from 5 to 24 carbon atoms as necessary to complete a fused heteroaromatic ring of furyl, thienyl, pyridyl, quinolinyl or other heterocyclic systems;

Group 5: alkoxylamino, alkylamino, or arylamino of from 1 to 24 carbon atoms; and Group 6: fluorine, chlorine, bromine or cyano.

Illustrative examples include 9,10-di-(2-naphthyl) anthracene and 2-t-butyl-9,10-di-(2-naphthyl)anthracene.

Other anthracene derivatives can be useful as a host in the LEL, including derivatives of 9,10-bis[4-(2,2-diphenylethenyl)phenyl]anthracene.

Benzazole derivatives (Formula G) constitute another class of useful host materials capable of supporting electroluminescence, and are particularly suitable for light emission of wavelengths longer than 400 run, e.g., blue, green, yellow, orange or red.

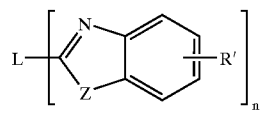

G wherein:

n is an integer of 3 to 8;

Z is O, NR or S; and

R and R' are individually hydrogen; alkyl of from 1 to 24 carbon atoms, for example, propyl, t-butyl, heptyl, and the like; aryl or hetero-atom substituted aryl of from 5 to 20 carbon atoms for example phenyl and naphthyl, furyl, thienyl, pyridyl, quinolinyl and other heterocyclic systems; or halo such as chloro, fluoro; or atoms necessary to complete a fused aromatic ring; and L is a linkage unit consisting of alkyl, aryl, substituted alkyl, or substituted aryl, which connects the multiple benzazoles together. L may be either conjugated with the multiple benzazoles or not in conjugation with them. An example of a useful benzazole is 2,2',2''-(1,3,5-phenylene)tris[1-phenyl-1H-benzimidazole].

Styrylarylene derivatives as described in U.S. Pat. No. 5,121,029 and JP 08333569 are also useful hosts for blue emission. For example, 9,10-bis[4-2,2-diphenylethenyl) phenyl]anthracene and 4,4'-bis(2,2-diphenylethenyl)-1,1'-biphenyl (DPVBi) are useful hosts for blue emission.

Useful fluorescent emitting materials include, but are not limited to, derivatives of anthracene, tetracene, xanthene, perylene, rubrene, coumarin, rhodamine, and quinacridone, dicyanomethylenepyran compounds, thiopyran compounds, polymethine compounds, pyrylium and thiapyrylium compounds, fluorene derivatives, periflanthene derivatives, indenoperylene derivatives, bis(azinyl)amine boron compounds, bis(azinyl)methane compounds, and carbostyryl compounds. Illustrative examples of useful materials include, but are not limited to, the following:

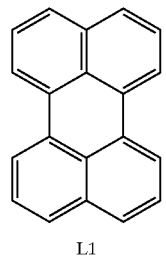

L1

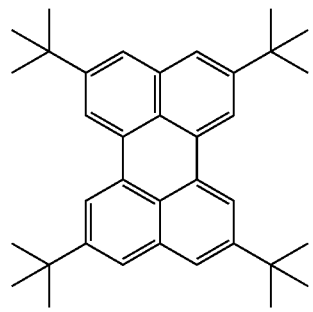

L2

-continued
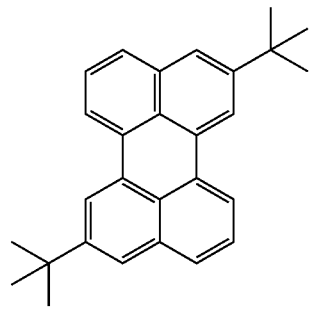
L3
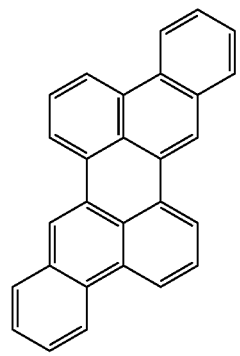
L4
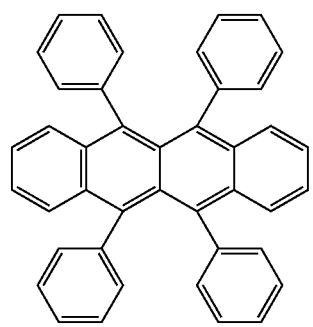
L5
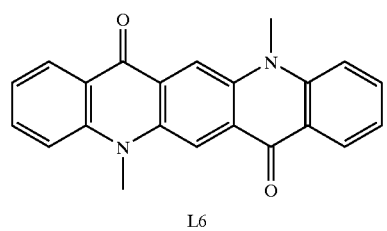
L6
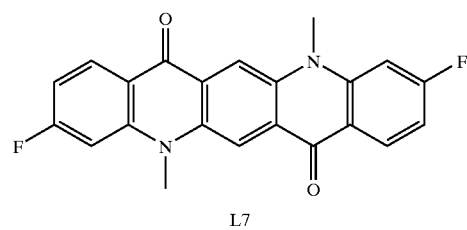
L7
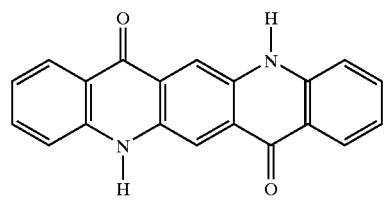
L8
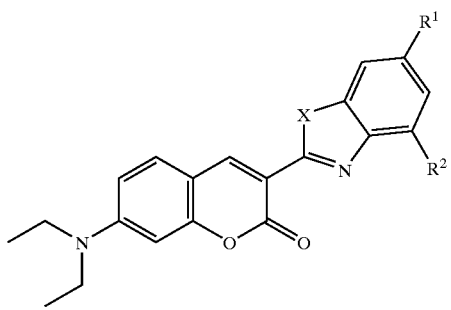
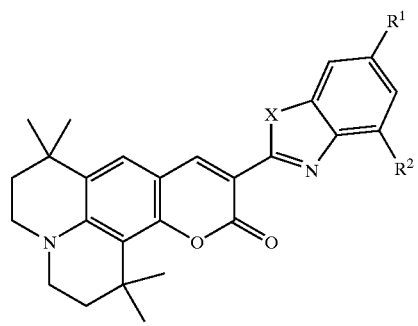
|     | X | R1     | R2     |     | X | R1     | R2     |
| --- | - | ------ | ------ | --- | - | ------ | ------ |
| L9  | O | H      | H      | L23 | O | H      | H      |
| L10 | O | H      | Methyl | L24 | O | H      | Methyl |
| L11 | O | Methyl | H      | L25 | O | Methyl | H      |
| L12 | O | Methyl | Methyl | L26 | O | Methyl | Methyl |
| L13 | O | H      | t-butyl| L27 | O | H      | t-butyl|
| L14 | O | t-butyl| H      | L28 | O | t-butyl| H      |
| L15 | O | t-butyl| t-butyl| L29 | O | t-butyl| t-butyl|
| L16 | S | H      | H      | L30 | S | H      | H      |
| L17 | S | H      | Methyl | L31 | S | H      | Methyl |
| L18 | S | Methyl | H      | L32 | S | Methyl | H      |
| L19 | S | Methyl | Methyl | L33 | S | Methyl | Methyl |
| L20 | S | H      | t-butyl| L34 | S | H      | t-butyl|

-continued
| L21 | S | t-butyl | H |  | L35 | S | t-butyl | H |
| L22 | S | t-butyl | t-butyl |  | L36 | S | t-butyl | t-butyl |
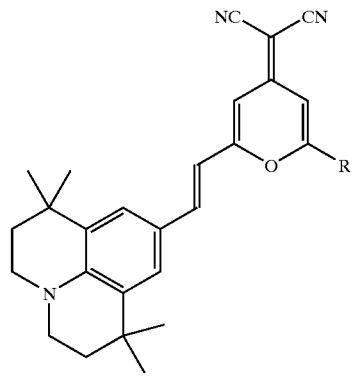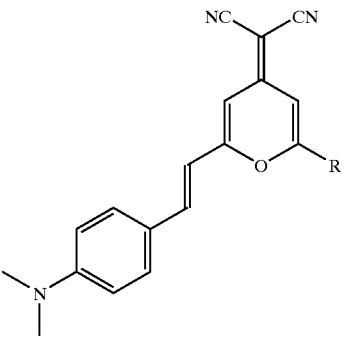
|  | R |  |  | R |
|---|---|---|---|---|
| L37 | phenyl | | L41 | phenyl |
| L38 | methyl | | L42 | methyl |
| L39 | t-butyl | | L43 | t-butyl |
| L40 | mesityl | | L44 | mesityl |
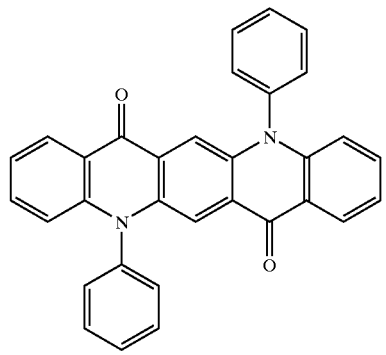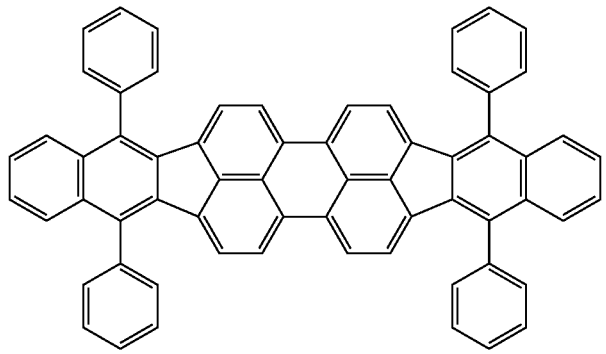
L45      L46
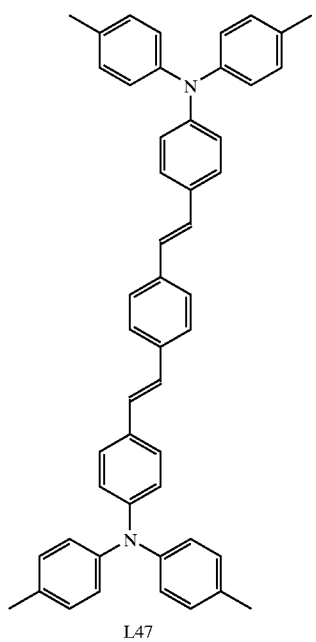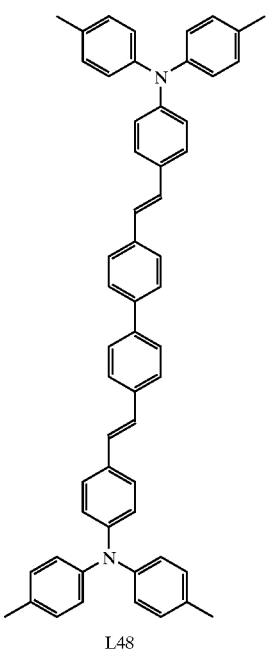
L47      L48

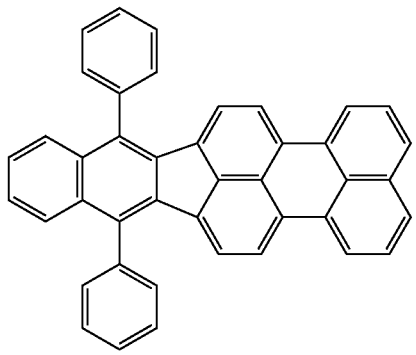

L49

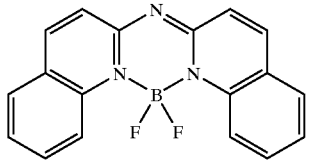

L50

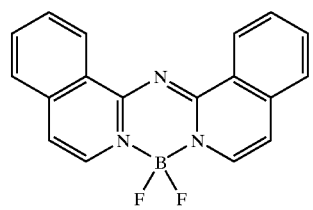

L51

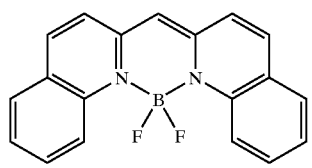

L52

In addition to the light-emitting materials of this invention, light-emitting phosphorescent materials may be used in the EL device. For convenience, the phosphorescent complex guest material may be referred to herein as a phosphorescent material. The phosphorescent material typically includes one or more ligands, for example monoanionic ligands that can be coordinated to a metal through an $SP^2$ carbon and a heteroatom. Conveniently, the ligand can be phenylpyridine (ppy) or derivatives or analogs thereof. Examples of some useful phosphorescent organometallic materials include tris(2-phenylpyridinato-N,$C^{2'}$)iridium(III), bis(2-phenylpyridinato-N,$C^{2'}$)iridium(III)(acetylacetonate), and bis(2-phenylpyridinato-N,$C^{2'}$)platinum(II). Usefully, many phosphorescent organometallic materials emit in the green region of the spectrum, that is, with a maximum emission in the range of 510 to 570 nm.

Phosphorescent materials may be used singly or in combinations other phosphorescent materials, either in the same or different layers. Phosphorescent materials and suitable hosts are described in WO 00/57676, WO 00/70655, WO 01/41512 A1, WO 02/15645 A1, US 2003/0017361 A1, WO 01/93642 A1, WO 01/39234 A2, U.S. Pat. No. 6,458,475 B1, WO 02/071813 A1, U.S. Pat. No. 6,573,651 B2, US 2002/0197511 A1, WO 02/074015 A2, U.S. Pat. No. 6,451,455 B1, US 2003/0072964 A1, US 2003/0068528 A1, U.S. Pat. No. 6,413,656 B1, U.S. Pat. No. 6,515,298 B2, U.S. Pat. No. 6,451,415 B1, U.S. Pat. No. 6,097,147, US 2003/0124381 A1, US 2003/0059646 A1, US 2003/0054198 A1, EP 1 239 526 A2, EP 1 238 981 A2, EP 1 244 155 A2, US 2002/0100906 A1, US 2003/0068526 A1, US 2003/0068535 A1, JP 2003073387A, JP 2003 073388A, US 2003/0141809 A1, US 2003/0040627 A1, JP 2003059667A, JP 2003073665A, and US 2002/0121638 A1.

The emission wavelengths of cyclometallated Ir(RI) complexes of the type $IrL_3$ and $IrL_2L'$, such as the green-emitting fac-tris(2-phenylpyridinato-N,$C^{2'}$)iridium(III) and bis(2-phenylpyridinato-N,$C^{2'}$)iridium(III)(acetylacetonate) may be shifted by substitution of electron donating or withdrawing groups at appropriate positions on the cyclometallating ligand L, or by choice of different heterocycles for the cyclometallating ligand L. The emission wavelengths may also be shifted by choice of the ancillary ligand L'. Examples of red emitters are the bis(2-(2'-benzothienyl)pyridinato-N, $C^{3'}$)iridium(III)(acetylacetonate) and tris(2-phenylisoquinolinato-N,C)iridium(III). A blue-emitting example is bis(2-(4,6-difluorophenyl)-pyridinato-N, $C^{2'}$iridium(III) (picolinate).

Red electrophosphorescence has been reported, using bis(2-(2'-benzo[4,5-a]thienyl)pyridinato-N, $C^3$) iridium (acetylacetonate) [$Btp_2Ir(acac)$] as the phosphorescent material (C. Adachi, S. Lamansky, M. A. Baldo, R. C. Kwong, M. E. Thompson, and S. R. Forrest, *App. Phys. Lett.*, 78, 1622–1624 (2001)).

Other important phosphorescent materials include cyclometallated Pt(II) complexes such as cis-bis(2-phenylpyridinato-N,$C^{2'}$)platinum(II), cis-bis(2-(2'-thienyl) pyridinato-N,$C^{3'}$) platinum(II), cis-bis(2-(2'-thienyl) quinolinato-N,$C^{5'}$) platinum(II), or (2-(4,6-difluorophenyl) pyridinato-N,$C^{2'}$) platinum (II) (acetylacetonate). Pt (II) porphyrin complexes such as 2,3,7,8,12,13,17,18-octaethyl-21H, 23H-porphine platinum(II) are also useful phosphorescent materials.

Still other examples of useful phosphorescent materials include coordination complexes of the trivalent lanthanides such as $Tb^{3+}$ and $Eu^{3+}$ (J. Kido et al., *Appl. Phys. Lett.*, 65, 2124 (1994)).

Suitable host materials for phosphorescent materials should be selected so that transfer of a triplet exciton can occur efficiently from the host material to the phosphorescent material but cannot occur efficiently from the phosphorescent material to the host material. Therefore, it is highly desirable that the triplet energy of the phosphorescent material be lower than the triplet energy of the host. Generally speaking, a large triplet energy implies a large optical bandgap. However, the band gap of the host should not be chosen so large as to cause an unacceptable barrier to injection of charge carriers into the light-emitting layer and an unacceptable increase in the drive voltage of the OLED. Suitable host materials are described in WO 00/70655 A2; 01/39234 A2; 01/93642 A1; 02/074015 A2; 02/15645 A1, and US 20020117662. Suitable hosts include certain aryl amines, triazoles, indoles and carbazole compounds. Examples of desirable hosts are 4,4'-N,N'-dicarbazole-biphenyl, otherwise known as 4,4'-bis(carbazol-9-yl) biphenyl or CBP; 4,4'-N,N'-dicarbazole-2,2'-dimethyl-biphenyl, otherwise known as 2,2'-dimethyl-4,4'-bis (carbazol-9-yl)biphenyl or CDBP; 1,3-bis(N,N'-dicarbazole)benzene, otherwise known as 1,3-bis(carbazol-9-yl)benzene, and poly(N-vinylcarbazole), including their derivatives.

Desirable host materials are capable of forming a continuous film.

Hole-Blocking Layer (HBL)

In addition to suitable hosts, an OLED device employing a phosphorescent material often requires at least one hole-blocking layer placed between the electron-transporting layer 111 and the light-emitting layer 109 to help confine the excitons and recombination events to the light-emitting layer comprising the host and phosphorescent material. In this case, there should be an energy barrier for hole migration from the host into the hole-blocking layer, while electrons should pass readily from the hole-blocking layer into the light-emitting layer comprising a host and a phosphorescent material. The first requirement entails that the ionization potential of the hole-blocking layer be larger than that of the light-emitting layer 109, desirably by 0.2 eV or more. The second requirement entails that the electron affinity of the hole-blocking layer not greatly exceed that of the light-emitting layer 109, and desirably be either less than that of light-emitting layer or not exceed that of the light-emitting layer by more than about 0.2 eV.

When used with an electron-transporting layer whose characteristic luminescence is green, such as an Alq-containing electron-transporting layer as described below, the requirements concerning the energies of the highest occupied molecular orbital (HOMO) and lowest unoccupied molecular orbital (LUMO) of the material of the hole-blocking layer frequently result in a characteristic luminescence of the hole-blocking layer at shorter wavelengths than that of the electron-transporting layer, such as blue, violet, or ultraviolet luminescence. Thus, it is desirable that the characteristic luminescence of the material of a hole-blocking layer be blue, violet, or ultraviolet. It is further desirable, but not absolutely required, that the triplet energy of the hole-blocking material be greater than that of the phosphorescent material. Suitable hole-blocking materials are described in WO 00/70655A2 and WO 01/93642 A1. Two examples of useful hole-blocking materials are bathocuproine (BCP) and bis(2-methyl-8-quinolinolato)(4-phenylphenolato) aluminum(III) (BAlq). The characteristic luminescence of BCP is in the ultraviolet, and that of BAlq is blue. Metal complexes other than BAlq are also known to block holes and excitons as described in US 20030068528. In addition, US 20030175553 A1 describes the use of fac-tris(1-phenylpyrazolato-N,$C^{2'}$)iridium(III) (Irppz) for this purpose.

When a hole-blocking layer is used, its thickness can be between 2 and 100 nm and suitably between 5 and 10 nm.

Electron-Transporting Layer (ETL)

Desirable thin film-forming materials for use in forming the electron-transporting layer 111 of the organic EL devices of this invention are metal-chelated oxinoid compounds, including chelates of oxine itself (also commonly referred to as 8-quinolinol or 8-hydroxyquinoline). Such compounds help to inject and transport electrons, exhibit high levels of performance, and are readily fabricated in the form of thin films. Exemplary of contemplated oxinoid compounds are those satisfying structural formula (E), previously described.

Other electron-transporting materials suitable for use in the electron-transporting layer 111 include various butadiene derivatives as disclosed in U.S. Pat. No. 4,356,429 and various heterocyclic optical brighteners as described in U.S. Pat. No. 4,539,507. Benzazoles satisfying structural formula (G) are also useful electron transporting materials. Triazines are also known to be useful as electron transporting materials.

If both a hole-blocking layer and an electron-transporting layer 111 are used, electrons should pass readily from the electron-transporting layer 111 into the hole-blocking layer. Therefore, the electron affinity of the electron-transporting layer 111 should not greatly exceed that of the hole-blocking layer. Desirably, the electron affinity of the electron-transporting layer should be less than that of the hole-blocking layer or not exceed it by more than about 0.2 eV.

If an electron-transporting layer is used, its thickness may be between 2 and 100 nm and suitably between 5 and 20 nm.

Other Useful Organic Layers and Device Architecture

In some instances, layers 109 through 111 can optionally be collapsed into a single layer that serves the function of supporting both light emission and electron transportation. The hole-blocking layer, when present, and layer 111 may also be collapsed into a single layer that functions to block holes or excitons, and supports electron transport. It also known in the art that emitting materials may be included in the hole-transporting layer 107. In that case, the hole-transporting material may serve as a host. Multiple materials may be added to one or more layers in order to create a white-emitting OLED, for example, by combining blue- and yellow-emitting materials, cyan- and red-emitting materials, or red-, green-, and blue-emitting materials. White-emitting devices are described, for example, in EP 1 187 235, US 20020025419, EP 1 182 244, U.S. Pat. No. 5,683,823, U.S. Pat. No. 5,503,910, U.S. Pat. No. 5,405,709, and U.S. Pat. No. 5,283,182 and can be equipped with a suitable filter arrangement to produce a color emission.

This invention may be used in so-called stacked device architecture, for example, as taught in U.S. Pat. No. 5,703,436 and U.S. Pat. No. 6,337,492.

Deposition of Organic Layers

The organic materials mentioned above are suitably deposited by any means suitable for the form of the organic materials. In the case of small molecules, they are conveniently deposited through sublimation or evaporation, but can be deposited by other means such as coating from a solvent together with an optional binder to improve film formation. If the material is a polymer, solvent deposition is usually preferred. The material to be deposited by sublimation or evaporation can be vaporized from a sublimator "boat" often comprised of a tantalum material, e.g., as described in U.S. Pat. No. 6,237,529, or can be first coated onto a donor sheet and then sublimed in closer proximity to the substrate. Layers with a mixture of materials can utilize separate sublimator boats or the materials can be pre-mixed and coated from a single boat or donor sheet. Patterned deposition can be achieved using shadow masks, integral shadow masks (U.S. Pat. No. 5,294,870), spatially-defined thermal dye transfer from a donor sheet (U.S. Pat. No. 5,688,551, U.S. Pat. No. 5,851,709 and U.S. Pat. No. 6,066,357) or an inkjet method (U.S. Pat. No. 6,066,357).

Encapsulation

Most OLED devices are sensitive to moisture or oxygen, or both, so they are commonly sealed in an inert atmosphere such as nitrogen or argon, along with a desiccant such as alumina, bauxite, calcium sulfate, clays, silica gel, zeolites, alkaline metal oxides, alkaline earth metal oxides, sulfates, or metal halides and perchlorates. Methods for encapsulation and desiccation include, but are not limited to, those described in U.S. Pat. No. 6,226,890. In addition, barrier layers such as $SiO_x$, Teflon, and alternating inorganic/polymeric layers are known in the art for encapsulation. Any of these methods of sealing or encapsulation and desiccation can be used with the EL devices constructed according to the present invention.

Optical Optimization

OLED devices of this invention can employ various well-known optical effects in order to enhance their emissive properties if desired. This includes optimizing layer thicknesses to yield maximum light transmission, providing dielectric mirror structures, replacing reflective electrodes with light-absorbing electrodes, providing anti-glare or anti-reflection coatings over the display, providing a polarizing medium over the display, or providing colored, neutral density, or color-conversion filters over the display. Filters, polarizers, and anti-glare or anti-reflection coatings may be specifically provided over the EL device or as part of the EL device.

Embodiments of the invention can provide advantageous features such as higher luminous yield, lower drive voltage, and higher power efficiency. Embodiments of the compounds useful in the invention can provide a wide range of hues including those useful in the emission of white light (directly or through filters to provide multicolor displays). Embodiments of the invention can also provide an area lighting device.

The invention and its advantages can be better appreciated by the following examples.

Synthetic Example: Preparation of Inv-2

The precursor to Inv-2, (2-quinolinyl)-2-benzothiazoleacetonitrile, was prepared by the following procedure. To a solution of 2-benzothiazoleacetonitrile (3.26 g, 18.7 mmol) in toluene (78 mL) was added slowly NaH (1.5 g of 60% oil dispersion, 37.4 mmol). The reaction mixture was stirred at ambient temperature until gas evolution was no longer evident. Neat 2-chloroquinoline (3.06 g, 18.7 mmol) was added to the reaction flask, and the reaction mixture was then heated at reflux for 24 h. The reaction mixture was cooled to ambient temperature, diluted with THF (50 mL), and quenched with $H_2O$ (100 mL). The aqueous portion was extracted with dichloromethane. The combined organics were washed with 1N HCl, and then saturated aqueous solution of $NaHCO_3$, dried over $MgSO_4$ and the volatile components were removed with a rotary evaporator. The resulting solid was slurried and washed with a 1:1 mixture of ether and heptane to afford 14.7 g (57.6%) of product. Results of $^1$H NMR spectroscopy and electrospray mass spectroscopy are consistent with the product.

Inv-2 was prepared by the following procedure. A mixture of (2-quinolinyl)-2-benzothiazoleacetonitrile (1.00 g, 3.3 mmol), diisoproylethylamine (2.74 mL, 16 mmol) $BF_3$-etherate, and dichloromethane (20 mL) were placed in a sealed pressure bottle and heated in an oil bath heated at 105° C. over night. The reaction mixture was cooled in an ice bath. The solid was collected by filtration and washed with dichloromethane. The concentrated filtrate was passed through a pad of silica gel (dichloromethane eluent) and concentrated. The two product samples were analyzed by TLC and $^1$H NMR spectroscopy, judged to be equivalent, and combined to afford Inv-2 (difluoro[1,2-dihydro-2[(2-benzothiazole-κN)cyanomethine]quinolinato-κN]boron, 0.98 g, 84%)). The sample was sublimed under reduced pressure with a nitrogen flow at 0.75 mTorr and 210° C., prior to OLED device fabrication.

Example of Maximum Emission and Luminance Efficiency

Emission spectra were obtained for a series of the above inventive examples and the following comparative examples.

| Example | Structure |
|---------|-----------|
| Comp-1 | 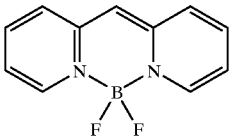 |
| Comp-2 | 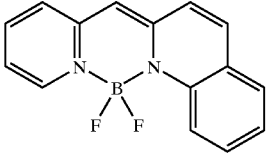 |
| Comp-3 | 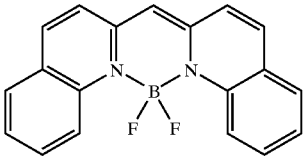 |

The emission spectra were obtained at room temperature in ethyl acetate solution at concentrations of $10^{-5}$ to $10^{-6}$ and expressed as quanta per unit time per unit wavelength interval against wavelength. A fluorescence procedure is well known to those skilled in the art [see, for example, C. A. Parker and W. T. Rees, Analyst, 85, 587 (1960)]. The maximum of emission spectra is defined as the wavelength corresponding to the highest point of such spectrum. The results are shown in the following table.

TABLE 1

Solution (EtOAc) data.

| Example | Type | Wavelength of Maximum Emission (nm) | Quantum Yield. |
|---------|------|-------------------------------------|----------------|
| Comp-1 | Comparative | 492 | 0.15 |
| Comp-2 | Comparative | 498 | 0.63 |
| Comp-3 | Comparative | 520 | 0.96 |
| Inv-1 | Inventive | 456 | 0.97 |
| Inv-2 | Inventive | 470 | 0.94 |
| Inv-3 | Inventive | 474 | 0.89 |
| Inv-4 | Inventive | 498 | 0.90 |
| Inv-22 | Inventive | 492 | 0.92 |
| Inv-23 | Inventive | 512 | 0.79 |
| Inv-27 | Inventive | 488 | 0.87 |

TABLE 1-continued

Solution (EtOAc) data.

| Example | Type | Wavelength of Maximum Emission (nm) | Quantum Yield. |
|---|---|---|---|
| Inv-29 | Inventive | 474 | 0.66 |
| Inv-30 | Inventive | 480 | 0.89 |

The above table shows that comparative compounds, Comp-1 and Comp-2, have desirable blue-green emission wavelengths, but have lower efficiency as shown by the quantum yield. The use of Comp-3 affords a high efficiency, but the emission wavelength of 520 nm is less desirable. However, the compounds in accordance with this invention have high efficiencies and desirable emission wavelengths.

Device Example 1-EL Device Fabrication of Samples 1–5

An EL device (Sample 1) satisfying the requirements of the invention was constructed in the following manner:

1. A glass substrate coated with an 85 nm layer of indium-tin oxide (ITO) as the anode was sequentially ultrasonicated in a commercial detergent, rinsed in deionized water, degreased in toluene vapor and exposed to oxygen plasma for about 1 min.

2. Over the ITO was deposited a 1 m fluorocarbon (CFx) hole-injecting layer (HIL) by plasma-assisted deposition of $CHF_3$.

3. A hole-transporting layer (HTL) of N,N'-di-1-naphthyl-N,N'-diphenyl-4,4'-diaminobiphenyl (NPB) having a thickness of 75 nm was then evaporated from a tantalum boat.

4. A 20 nm light-emitting layer (LEL) of 2-tert-butyl-9,10-di-(2-naphthyl)anthracene (TBADN) and Inv-27 (0.50 wt %) were then deposited onto the hole-transporting layer. These materials were also evaporated from tantalum boats.

5. A 35 nm electron-transporting layer (ETL) of tris(8-quinolinolato)aluminum (III) ($AlQ_3$) was then deposited onto the light-emitting layer. This material was also evaporated from a tantalum boat.

6. On top of the $AlQ_3$ layer was deposited a 220 nm cathode formed of a 10:1 volume ratio of Mg and μg.

The above sequence completed the deposition of the EL device. The device was then hermetically packaged in a dry glove box for protection against ambient environment.

EL devices, Samples 2, 3, and 4, incorporating Inv-27 were fabricated in an identical manner as Sample 1 but Inv-27 was used at the levels indicated in the Table 2. Sample 5 was constructed in the same manner as Sample 1 except Inv-27 was omitted. The cells thus formed were tested for efficiency and color at an operating current of 20 mA/cm² and the results are reported in Table 2 in the form of output efficiency (W/A), luminance yield (cd/A), maximum wavelength (λmax) of emission and CIE (Commission Internationale de L'Eclairage) coordinates.

TABLE 2

Evaluation Results for EL devices.

| Sample | Level (%) | Efficiency (W/A) | Yield (cd/A) | CIEx | CIEy | Emission λmax (nm) | Type |
|---|---|---|---|---|---|---|---|
| 1 | 0.50 | 0.046 | 5.52 | 0.226 | 0.545 | 496 | Invention |
| 2 | 1.00 | 0.048 | 6.04 | 0.229 | 0.575 | 496 | Invention |
| 3 | 1.50 | 0.047 | 6.11 | 0.240 | 0.586 | 496 | Invention |
| 4 | 2.00 | 0.046 | 5.93 | 0.244 | 0.588 | 500 | Invention |
| 5 | 0.00 | 0.037 | 1.56 | 0.159 | 0.128 | 452 | Comparison |

As can be seen from Table 2, all tested EL devices incorporating the invention dopant demonstrated superior color relative to the comparative device without the dopant. These doped EL devices exhibit blue-green electroluminescence.

Device Example 2-EL Device Fabrication of Samples 6–12

EL devices, Samples 6 through 12 were fabricated in an identical manner as Sample 1, but Inv-27 was replaced with Inv-2, Inv-3, Inv-4, Inv-22, Inv-23, Inv-29 and Inv-30 respectively. The levels at which these materials were used are indicated in Table 3. The cells thus formed were tested for efficiency and color at an operating current of 20 mA/cm² and the results are reported in Table 3 in the form of output efficiency (W/A), luminance yield (cd/A), maximum wavelength (λmax) of emission and CIE coordinates.

TABLE 3

Evaluation Results for EL devices.

| Sample | Material | Level (%) | Efficiency (W/A) | Yield (cd/A) | CIEx | CIEy | Emission λmax (nm) | Type |
|---|---|---|---|---|---|---|---|---|
| 6 | Inv-2 | 1.0 | 0.041 | 4.43 | 0.218 | 0.455 | 480 | Invention |
| 7 | Inv-3 | 2.0 | 0.050 | 5.61 | 0.207 | 0.499 | 484 | Invention |

TABLE 3-continued

Evaluation Results for EL devices.

| Sample | Material | Level (%) | Efficiency (W/A) | Yield (cd/A) | CIEx | CIEy | Emission λmax (nm) | Type |
|---|---|---|---|---|---|---|---|---|
| 8 | Inv-4 | 2.0 | 0.050 | 7.00 | 0.264 | 0.599 | 504 | Invention |
| 9 | Inv-22 | 1.5 | 0.051 | 6.77 | 0.249 | 0.599 | 500 | Invention |
| 10 | Inv-23 | 0.5 | 0.046 | 6.92 | 0.320 | 0.564 | 520 | Invention |
| 11 | Inv-29 | 0.5 | 0.042 | 4.04 | 0.185 | 0.425 | 480 | Invention |
| 12 | Inv-30 | 1.0 | 0.058 | 6.71 | 0.208 | 0.526 | 488 | Invention |

As can be seen from Table 3, the EL devices offer a range of hues including blue, blue-green, and green electroluminescence.

Device Example 3-EL Device Fabrication of Samples 13 and 14

An EL device (Sample 13) satisfying the requirements of the invention was constructed in the following manner:

1. A glass substrate coated with an 85 nm layer of indium-tin oxide (ITO) as the anode was sequentially ultrasonicated in a commercial detergent, rinsed in deionized water, degreased in toluene vapor and exposed to oxygen plasma for about 1 min.
2. Over the ITO was deposited a 1 nm fluorocarbon (CFx) hole-injecting layer (HIL) by plasma-assisted deposition of $CHF_3$.
3. A hole-transporting layer (HTL) of N,N'-di-1-naphthyl-N,N'-diphenyl-4,4'-diaminobiphenyl (NPB) having a thickness of 150 nm was then evaporated from a tantalum boat.
4. A 20 nm first light-emitting layer (LEL-1) of 2-tert-butyl-9,10-di-(2-naphthyl)anthracene (TBADN) and Inv-3 (1.0 wt. %) were then deposited onto the hole-transporting layer. These materials were also evaporated from tantalum boats.
5. A 20 nm second light-emitting layer (LEL-2) of tris(8-quinolinolato)aluminum (III) ($AlQ_3$) and yellow dopant, 6,11-diphenyl-5, 12-bis(4-(6-methyl-benzothiazol-2-yl)phenyl)naphthacene (DBzR, 2.5 wt. %), was then deposited onto the first light-emitting layer. This material was also evaporated from a tantalum boat.
6. A 35 nm electron-transporting layer (ETL) of tris(8-quinolinolato)aluminum (III) ($AlQ_3$) was then deposited onto the light-emitting layer. This material was also evaporated from a tantalum boat.
7. On top of the $AlQ_3$ layer was deposited a 220 nm cathode formed of a 10:1 volume ratio of Mg and Ag.

The above sequence completed the deposition of the EL device. The device was then hermetically packaged in a dry glove box for protection against ambient environment.

EL device, Sample 14, was fabricated in the same manner as Sample 13 except Inv-3 was used at 2.0 wt. %. The cells thus formed were tested for efficiency and color at an operating current of 20 mA/cm$^2$ and the results are reported in Table 4 in the form of output efficiency (W/A), luminance yield (cd/A) and CIE coordinates.

TABLE 4

Evaluation Results for EL devices.

| Sample | Level (%) | Efficiency (W/A) | Yield (cd/A) | CIEx | CIEy | Type |
|---|---|---|---|---|---|---|
| 13 | 1.0 | 0.058 | 7.41 | 0.460 | 0.472 | Invention |
| 14 | 2.0 | 0.060 | 7.73 | 0.461 | 0.477 | Invention |

It can be seen from Table 4 that the color of light emitted by a device having two light-emitting layers, one including Inv-3 and one including a yellow dopant, its suitable, after appropriate filtration, for the production of white light.

The entire contents of the patents and other publications referred to in this specification are incorporated herein by reference. The invention has been described in detail with particular reference to certain preferred embodiments thereof, but it will be understood that variations and modifications can be effected within the spirit and scope of the invention.

Parts List

101 Substrate
103 anode
105 hole-injecting layer (HIL)
107 hole-transporting layer (HTL)
109 light-emitting layer (LEL)
111 electron-transporting layer (ETL)
113 cathode

What is claimed is:

1. An electroluminescent device comprising a light emitting layer comprising a boron complex wherein the boron is bonded to a nitrogen atom of a 6-membered heteroaromatic ring group and to a nitrogen atom of a 5-membered heteroaromatic ring group, provided that the 5- and 6-membered heteroaromatic ring groups are further connected by a methene bridge to form a 6-membered ring, and provided further that the 5-membered heteroaromatic ring contains at least one additional heteroatom that is divalent or trivalent.

2. The device of claim 1, wherein the additional heteroatom is a N, O, S, Se, or Te atom.

3. The device of claim 1, wherein the additional heteroatom is a N, O or S atom.

4. The device of claim 1, wherein the five-membered ring is fused to an additional aromatic ring group.

5. The device of claim 1, wherein the five-membered ring is fused to an additional aromatic ring group and the six-membered ring is fused to an additional aromatic ring group.

6. The device of claim 1, wherein the methene bridge is substituted with cyano substituent, an aryl group, a heteroaryl group, or an alkyl group.

7. The device of claim 1, wherein the boron complex is represented by Formula (1),

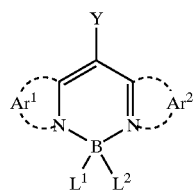

(1)

wherein:
Ar$^1$ represents the atoms necessary to form a six-membered heteroaromatic ring;
Ar$^2$ represents the atoms necessary to form a five-membered heteroaromatic ring that contains at least one additional heteroatom that is divalent or trivalent;
L$^1$ and L$^2$ represent independently selected substituents;
Y represents hydrogen or a substituent.

8. The device of claim 7, wherein, Ar$^1$ represents the atoms necessary to form pyridine ring group.

9. The device of claim 7, wherein, Ar$^2$ represents the atoms necessary to form an imidazole ring group, an oxazole ring group, a thiazole ring group, or a selenazole ring group.

10. The device of claim 7, wherein Y represents a cyano substituent, a trifluoromethyl substituent, an aryl group, a heteroaryl group, or an alkyl group.

11. The device of claim 7, wherein L$^1$ and L$^2$ represent fluoro substituents.

12. The device of claim 1, wherein the boron complex is represented by Formula (2),

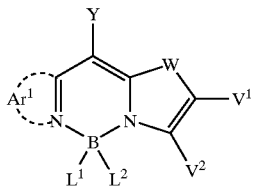

(2)

wherein:
W represents O, S, Se, or N-R$^a$, wherein R$^a$ is a substituent;
V$^1$ and V$^2$ independently represent hydrogen or an independently selected substituent, provided that V$^1$ and V$^2$ may join together to form a ring group;
Ar$^1$ represents the atoms necessary to form a six-membered heteroaromatic ring group;
L$^1$ and L$^2$ represent independently selected substituents;
Y represents hydrogen or a substituent.

13. The device of claim 12, wherein V$^1$ and V$^2$ independently represent an aryl group or an alkyl group.

14. The device of claim 12, wherein V$^1$ and V$^2$ join together to form an aromatic ring group.

15. The device of claim 1, wherein the boron complex is represented by Formula (3),

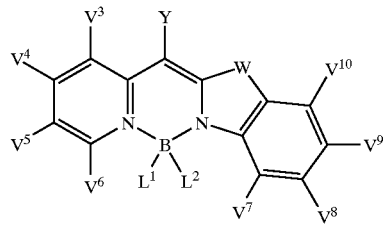

(3)

wherein:
W represents O, S, Se, or N-R$^a$, wherein R$^a$ is a substituent;
V$^3$–V$^{10}$ independently represent hydrogen or an independently selected substituent, provided that adjacent substituents may join together to form a ring group;
L$^1$ and L$^2$ represent independently selected substituents;
Y represents hydrogen or a substituent.

16. The device of claim 15, wherein W represents S.

17. The device of claim 15, wherein L$^1$ and L$^2$ represent fluoro substituents.

18. The device of claim 15, wherein, independently, at least two of V$^3$–V$^6$ and at least two of V$^7$–V$^{10}$ combine to form independently selected ring groups.

19. The device of claim 1 wherein the layer comprises a host and dopant where the dopant is present in an amount of up to 10 wt % of the host.

20. The device of claim 1 wherein the host material is represented by Formula (4),

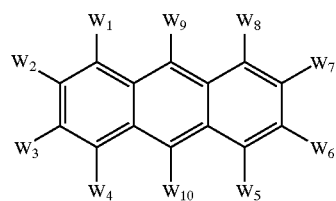

(4)

wherein:
W$_1$–W$_{10}$ independently represent hydrogen or an independently selected substituent, provided that two adjacent substituents can combine to form rings.

21. The device of claim 20 wherein W$^9$ and W$^{10}$ independently represent naphthyl groups.

22. The device of claim 20 wherein W$^9$ and W$^{10}$ represent a naphthyl group and a biphenyl group.

23. The device of claim 20 wherein W$^9$ represents a biphenyl group.

24. The device of claim 1 wherein the boron complex is between 0.5 and 8% by volume of the light-emitting layer.

25. A display comprising the electroluminescent device of claim 1.

26. The device of claim 1 wherein white light is produced either directly or by using filters.

27. An area lighting device comprising the electroluminescent device of claim 1.

28. A process for emitting light comprising applying a potential across the device of claim 1.

* * * * *